United States Patent
Bunda et al.

(10) Patent No.: US 7,345,083 B2
(45) Date of Patent: Mar. 18, 2008

(54) HYDROISOINDOLINE TACHYKININ RECEPTOR ANTAGONISTS

(75) Inventors: Jaime Lynn Bunda, Holland, PA (US); Robert J. DeVita, Westfield, NJ (US); Jinlong Jiang, Scotch Plains, NJ (US); Sander G. Mills, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 11/714,352

(22) Filed: Mar. 6, 2007

(65) Prior Publication Data

US 2007/0161695 A1 Jul. 12, 2007

Related U.S. Application Data

(62) Division of application No. 11/043,213, filed on Jan. 26, 2005, now Pat. No. 7,217,731.

(60) Provisional application No. 60/561,227, filed on Apr. 9, 2004, provisional application No. 60/539,913, filed on Jan. 27, 2004.

(51) Int. Cl.
*A61K 31/4035* (2006.01)
*C07D 209/44* (2006.01)

(52) U.S. Cl. .................................. 514/415; 548/512
(58) Field of Classification Search ................ 548/512; 514/415
See application file for complete search history.

(56) References Cited

FOREIGN PATENT DOCUMENTS

WO    WO 97/141671    *    4/1997
WO    WO 2005/032464 A2    4/2005

OTHER PUBLICATIONS

Co-pending U.S. Appl. No. 10/586,727, filed Jul. 18, 2006.

* cited by examiner

*Primary Examiner*—Kamal A. Saeed
*Assistant Examiner*—Janet L. Coppins
(74) *Attorney, Agent, or Firm*—Curtis C. Panzer; Valerie J. Camara

(57) ABSTRACT

The present invention is directed to certain hydroisoindoline compounds which are useful as neurokinin-1 (NK-1) receptor antagonists, and inhibitors of tachykinin and in particular substance P. The invention is also concerned with pharmaceutical formulations comprising these compounds as active ingredients and the use of the compounds and their formulations in the treatment of certain disorders, including emesis, urinary incontinence, depression, and anxiety.

7 Claims, No Drawings

HYDROISOINDOLINE TACHYKININ RECEPTOR ANTAGONISTS

CROSS-REFERENCE TO RELATED APPLICATIONS

This application is a divisional application of U.S. application Ser. No. 11/043,213, filed Jan. 26, 2005, now U.S. Pat. No. 7,217,731, which claims priority to U.S. Provisional Application Nos. 60/539,913, filed Jan. 27, 2004 and 60/561,227, filed Apr. 9, 2004.

BACKGROUND OF THE INVENTION

Substance P is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence. In addition to substance P, the known mammalian tachykinins include neurokinin A and neurokinin B. The current nomenclature designates the receptors for substance P, neurokinin A, and neurokinin B as neurokinin-1 (NK-1), neurokinin-2 (NK-2), and neurokinin-3 (NK-3), respectively.

Tachykinin, and in particular substance P, antagonists are useful in the treatment of clinical conditions which are characterized by the presence of an excess of tachykinin, in particular substance P, activity, including disorders of the central nervous system, nociception and pain, gastrointestinal disorders, disorders of bladder function and respiratory diseases.

SUMMARY OF THE INVENTION

The present invention is directed to certain hydroisoindoline compounds which are useful as neurokinin-1 (NK-1) receptor antagonists, and inhibitors of tachykinin and in particular substance P. The invention is also concerned with pharmaceutical formulations comprising these compounds as active ingredients and the use of the compounds and their formulations in the treatment of certain disorders, including emesis, urinary incontinence, depression, and anxiety.

DETAILED DESCRIPTION OF THE INVENTION

The present invention is directed to compounds of the formula I:

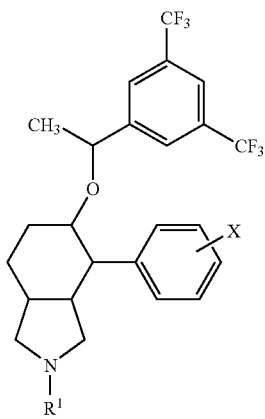

I wherein:
$R^1$ is selected from the group consisting of:
(1) hydrogen,
(2) $C_{1-6}$alkyl, which is unsubstituted or substituted with halogen, hydroxyl or phenyl,
(3) cyclopentenone, which is unsubstituted or substituted with hydroxyl or methyl,
(4) —(CO)—$C_{1-6}$alkyl,
(5) —(CO)—$NH_2$,
(6) —(CO)—$NHC_{1-6}$alkyl, and
(7) —(CO)—$N(C_{1-6}$alkyl)($C_{1-6}$alkyl);
X is independently selected from the group consisting of:
(1) hydrogen,
(2) fluorine, and
(3) methyl;
and pharmaceutically acceptable salts thereof and individual enantiomers and diastereomers thereof.

An embodiment of the present invention includes compounds of the formula Ia:

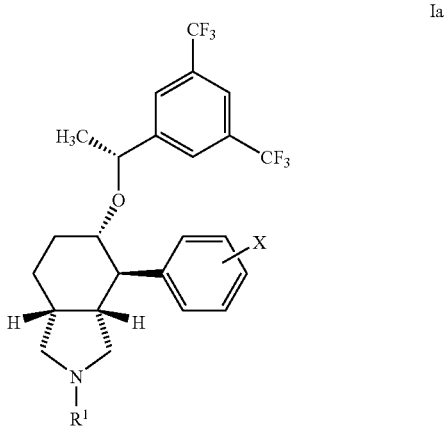

Ia wherein $R^1$ and X are defined herein;
and pharmaceutically acceptable salts thereof and individual enantiomers and diastereomers thereof.

An embodiment of the present invention includes compounds of the formula Ib:

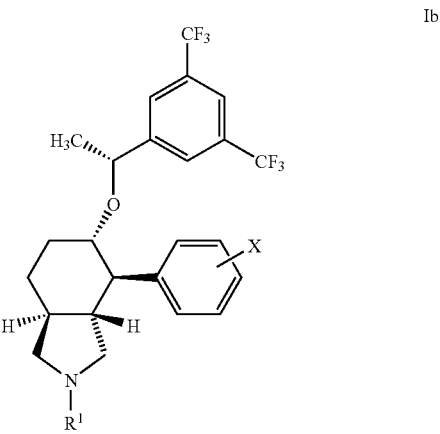

Ib wherein $R^1$ and X are defined herein;
and pharmaceutically acceptable salts thereof and individual enantiomers and diastereomers thereof.

An embodiment of the present invention includes compounds wherein $R^1$ is selected from the group consisting of:

(1) hydrogen,
(2) C$_{1-3}$alkyl, which is unsubstituted or substituted with hydroxyl or phenyl,
(3) cyclopent-2-en-1-one, which is unsubstituted or substituted with hydroxyl or methyl,
(4) —(CO)—C$_{1-3}$alkyl,
(5) —(CO)—NH$_2$,
(6) —(CO)—NHC$_{1-3}$alkyl, and
(7) —(CO)—N(C$_{1-3}$alkyl)(C$_{1-3}$alkyl).

Within this embodiment the present invention includes compounds wherein R$^1$ is selected from the group consisting of:
(1) hydrogen,
(2) methyl,
(3) 2-phenylethyl,
(4) 2-hydroxyethyl,
(5) cyclopent-2-en-1-one,
(6) 5-hydroxycyclopent-2-en-1-one,
(7) 4-hydroxycyclopent-2-en-1-one,
(8) 2-methylcyclopent-2-en-1-one,
(9) acetyl,
(10) acetamido,
(11) methyl-acetamido, and
(12) dimethyl-acetamido.

Further within this embodiment, the present invention is directed to compounds wherein R$^1$ is hydrogen.

Also further within this embodiment, the present invention is directed to compounds wherein R$^1$ is methyl, 2-phenylethyl or 2-hydroxyethyl.

Also further within this embodiment, the present invention is directed to compounds wherein R$^1$ is:

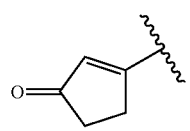

which is unsubstituted or substituted with hydroxyl or methyl.

Also further within this embodiment, the present invention is directed to compounds wherein R$^1$ is acetyl, acetamido, methyl-acetamido or dimethyl-acetamido.

An embodiment of the present invention includes compounds wherein X is hydrogen. An embodiment of the present invention includes compounds wherein X is fluorine. An embodiment of the present invention includes compounds wherein X is methyl.

Specific embodiments of the present invention include a compound which is selected from the group consisting of the subject compounds of the Examples herein and pharmaceutically acceptable salts thereof and individual enantiomers and diastereomers thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without preferred stereochemistry. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

There are several acceptable methods of naming the compounds discussed herein.

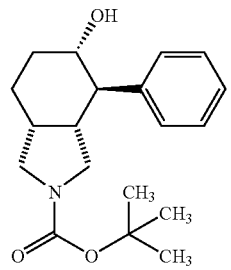

For example, the above compound can be named either as "(3aR,4R,5S,7aR) tert-butyl-5-hydroxy-4-phenyloctahydro-2H-isoindole-2-carboxylate" or "tert-butyl (3aR,4R,5S,7aR)-5-4-phenyloctahydro-2H-isoindole-2-carboxylate".

The core structure may be generally referred to as octahydroisoindole, hexahydroisoindoline, perhydroisoindoline, hydroisoindoline, or hydroisoindole compounds.

As appreciated by those of skill in the art, halo or halogen as used herein are intended to include fluoro, chloro, bromo and iodo. Similarly, C$_{1-6}$, as in C$_{1-6}$alkyl is defined to identify the group as having 1, 2, 3, 4, 5 or 6 carbons in a linear or branched arrangement, such that C$_{1-8}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The compounds of the present invention are useful in the prevention and treatment of a wide variety of clinical conditions which are characterized by the presence of an excess of tachykinin, in particular substance P, activity. Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis. Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia, frequent urination and urinary incontinence, including the prevention or treatment of overactive bladder with symptoms of urge urinary incontinence, urgency, and frequency; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine. The compounds of the present invention are also of value in the treatment of a combination of the above conditions, in particular in the treatment of combined post-operative pain and post-operative nausea and vomiting.

The compounds of the present invention are particularly useful in the prevention or treatment of emesis, including acute, delayed or anticipatory emesis, such as emesis induced by chemotherapy, radiation, toxins, pregnancy, vestibular disorders, motion, surgery, migraine, and variations in intercranial pressure. For example, the compounds of the present invention are of use optionally in combination with other antiemetic agents for the prevention of acute and delayed nausea and vomiting associated with initial and repeat courses of moderate or highly emetogenic cancer chemotherapy, including high-dose cisplatin. Most especially, the compounds of the present invention are of use in the treatment of emesis induced by antineoplastic (cytotoxic) agents, including those routinely used in cancer chemotherapy, and emesis induced by other pharmacological agents, for example, rolipram. Examples of such chemotherapeutic agents include alkylating agents, for example, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics. Particular examples of chemotherapeutic agents are described, for instance, by D. J. Stewart in *Nausea and Vomiting: Recent Research and Clinical Advances*, Eds. J. Kucharczyk et al, CRC Press Inc., Boca Raton, Fla., USA (1991) pages 177-203, especially page 188. Commonly used chemotherapeutic agents include cisplatin, dacarbazine (DTIC), dactinomycin, mechlorethamine, streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163-172]. A further aspect of the present invention comprises the use of a compound of the present invention for achieving a chronobiologic (circadian rhythm phase-shifting) effect and alleviating circadian rhythm disorders in a mammal. The present invention is further directed to the use of a compound of the present invention for blocking the phase-shifting effects of light in a mammal.

The present invention is further directed to the use of a compound of the present invention or a pharmaceutically acceptable salt thereof, for enhancing or improving sleep quality as well as preventing and treating sleep disorders and sleep disturbances in a mammal. In particular, the present invention provides a method for enhancing or improving sleep quality by increasing sleep efficiency and augmenting sleep maintenance. In addition, the present invention provides a method for preventing and treating sleep disorders and sleep disturbances in a mammal which comprising the administration of a compound of the present invention or a pharmaceutically acceptable salt thereof. The present invention is useful for the treatment of sleep disorders, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus, fibromyalgia, muscle pain, sleep apnea and restless legs and non specific REM disturbances as seen in ageing.

The particularly preferred embodiments of the instant invention are the treatment of emesis, urinary incontinence, depression or anxiety by administration of the compounds of the present invention to a subject (human or animal) in need of such treatment.

The present invention is directed to a method for the manufacture of a medicament for antagonizing the effect of substance P at its receptor site or for the blockade of neurokinin-1 receptors in a mammal comprising combining a compound of the present invention with a pharmaceutical carrier or diluent. The present invention is further directed to a method for the manufacture of a medicament for the treatment of a physiological disorder associated with an excess of tachykinins in a mammal comprising combining a compound of the present invention with a pharmaceutical carrier or diluent.

The present invention also provides a method for the treatment or prevention of physiological disorders associated with an excess of tachykinins, especially substance P, which method comprises administration to a patient in need thereof of a tachykinin reducing amount of a compound of the present invention or a composition comprising a compound of the present invention. As used herein, the term "treatment" or "to treat" refers to the administration of the compounds of the present invention to reduce, ameliorate, or eliminate either the symptoms or underlying cause of the noted disease conditions, in a subject (human or animal) that suffers from that condition or displays clinical indicators thereof. The term "prevention" or "to prevent" refers to the administration of the compounds of the present invention to reduce, ameliorate, or eliminate the risk or likelihood of occurrence of the noted disease conditions, in a subject (human or animal) susceptible or predisposed to that condition.

The compounds of this invention are useful for antagonizing tachykinins, in particular substance P in the treatment of gastrointestinal disorders, central nervous system disorders, inflammatory diseases, pain or migraine and asthma in a mammal in need of such treatment. This activity can be demonstrated by the following assays.

Receptor Expression in COS: To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electroporation in 800 ul of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100 U/ml penicillin-streptomycin, and 90% DMEM media (GIBCO, Grand Island, N.Y.) in 5% $CO_2$ at 37° C. for three days before the assay.

Stable Expression in CHO: To establish a stable cell line expressing the cloned human NK1R, the cDNA was subcloned into the vector pRcCMV (INVITROGEN). Transfection of 20 ug of the plasmid DNA into CHO cells was achieved by electroporation in 800 ul of transfection buffer supplemented with 0.625 mg/ml Herring sperm DNA at 300 V and 950 uF using the IBI GENEZAPPER (IBI). The transfected cells were incubated in CHO media [10% fetal calf serum, 100 U/ml penicillin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

Assay Protocol using COS or CHO: The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-SP and 20 ul of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter. The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1 N HCl is added. Each well is sonicated at 4° C. and extracted with $CHCl_3$/methanol (1:1). The aqueous phase is applied to a 1 ml Dowex AG 1×8 ion exchange column. The column is washed with 0.1 N formic acid followed by 0.025 M ammonium formate-0.1 N formic acid. The inositol monophosphate is eluted with 0.2 M ammonium formate-0.1 N formic acid and quantitated by beta counter. In particular, the intrinsic tachykinin receptor antagonist activities of the compounds of the present invention may be demonstrated by these assays. The compounds of the following examples have activity in the aforementioned assays in the range of 0.05 nM to 10 μM. The activity of the present compounds may also be demonstrated by the assay disclosed by Lei, et al., *British J. Pharmacol.*, 105, 261-262 (1992).

According to a further or alternative aspect, the present invention provides a compound of the present invention for use as a composition that may be administered to a subject in need of a reduction of the amount of tachykinin or substance P in their body.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives.

Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

The compositions containing compounds of the present invention may be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples in the pharmacy arts of unit dosage forms. The compositions containing compounds of the present invention may also be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individuals body in a therapeutically useful form and therapeutically effective amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The term "therapeutically effective amount" refers to a sufficient quantity of the compounds of the present invention, in a suitable composition, and in a suitable dosage form to treat or prevent the noted disease conditions.

The compounds of the present invention may be administered in combination with another substance that has a complimentary effect to the tachykinin and substance P inhibitors of the present invention. Accordingly, in the prevention or treatment of emesis, a compound of the present invention may be used in conjunction with other anti-emetic agents, especially $5HT_3$ receptor antagonists, such as ondansetron, granisetron, tropisetron, palenosetron and zatisetron, a corticosteroid, such as dexamethasone, or $GABA_B$ receptor agonists, such as baclofen. Likewise, for the prevention or treatment of migraine a compound of the present invention may be used in conjunction with other anti-migraine agents, such as ergotamines or $5HT_1$ agonists, especially sumatriptan, naratriptan, zolmatriptan or rizatriptan.

It will be appreciated that for the treatment of depression or anxiety, a compound of the present invention may be used in conjunction with other anti-depressant or anti-anxiety agents, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), α-adrenoreceptor antagonists, atypical anti-depressants, benzodiazepines, $5\text{-}HT_{1A}$ agonists or antagonists, especially $5\text{-}HT_{1A}$ partial agonists, corticotropin releasing factor (CRF) antagonists, and pharmaceutically acceptable salts thereof. For the treatment or prevention of eating disorders, including obesity, bulimia nervosa and compulsive eating disorders, a compound of the present invention may be used in conjunction with other anorectic agents. It will be appreciated that for the treatment or prevention of pain or nociception or inflammatory diseases, a compound of the present invention may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent.

It will be appreciated that when using any combination described herein, both the compound of the present invention and the other active agent(s) will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active component may be administered as a tablet and then, within a reasonable period of time, the second active component may be administered either as an oral dosage form such as a tablet or a fast-dissolving oral dosage form. By a "fast dissolving oral formulation" is meant, an oral delivery form which when placed on the tongue of a patient, dissolves within about 10 seconds. By "reasonable period of time" is meant a time period that is not in excess of about 1 hour. That is, for example, if the first active component is provided as a tablet, then within one hour, the second active component should be administered, either in the same type of dosage form, or another dosage form which provides effective delivery of the medicament.

The compounds of this invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of the conditions associated with an excess of tachykinins, a suitable dosage level of the compounds of the present invention, or pharmaceutically acceptable salts thereof, is about 0.001 to 50 mg/kg per day, in particular about 0.01 to about 25 mg/kg, such as from about 0.05 to about 10 mg/kg per day. The dosage range will generally be about 0.5 to 1000 mg per patient per day, which may be administered in single or multiple doses. Preferably, the dosage range will be about 0.5 mg to 500 mg per patient per day; more preferably about 0.5 mg to 200 mg per patient per day; and even more preferably about 5 mg to 50 mg per patient per day. Specific dosages of the compounds of the present invention, or pharmaceutically acceptable salts thereof, for administration include 1 mg, 5 mg, 10 mg, 30 mg, 100 mg, and 500 mg. Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific pharmaceutical compositions for treatment or prevention of excess tachykinins comprise about 1 mg, 5 mg, 10 mg, 30 mg, 100 mg, and 500 mg of active ingredient.

Several methods for preparing the compounds of this invention are illustrated in the following Examples. Starting materials and the requisite intermediates are in some cases commercially available, or can be prepared according to literature procedures or as illustrated herein. All $^1$H NMR spectra were obtained on instrumentation at a field strength of 400 or 500 MHz.

EXAMPLE 1

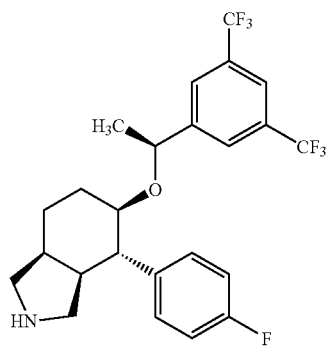

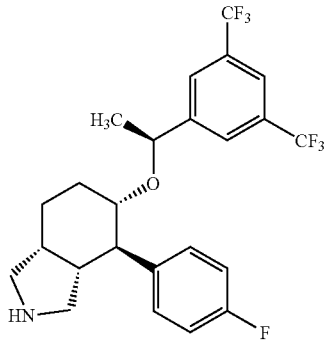

-continued (3aR,4R,5S,7aR)-5-{1(S)-[3,5-bis(Trifluoromethyl) phenyl]ethoxy}-4-(4-fluorophenyl)octahydro-1H-isoindole and (3aS,4S,5R,7aS)-5-{1(S)-[3,5-bis(Trifluoromethyl)phenyl]ethoxy}-4-(4-fluorophenyl) octahydro-1H-isoindole Step A:
2-(4-Fluorophenyl)-N-methoxy-N-methylacetamide To a solution of 16.7 g (108.4 mmol) (4-fluorophenyl) acetic acid in dry methylene chloride under nitrogen atmosphere was added 13.8 g (141.5 mmol) N,O-dimethylhydroxyl amine, 20 mL triethylamine, 14.2 g (119.3 mmol) 4-dimethylaminopyridine (DMAP) and 27 g (140.6 mmol) EDC. The reaction mixture was stirred at RT for 2 hr then transferred to a separatory funnel. The mixture was washed consecutively with 2 N aq. HCl, brine, saturated aq. NaHCO$_3$ and brine. The organic layer was dried over drying agent, filtered and the solvent evaporated under vacuum to give 21 g of the crude title compound which was used without further purification. $^1$H-NMR (CDCl$_3$): δ: 7.26 (2 H, m), 7.02 (2 H, m), 3.77 (2 H, s), 3.65 (3 H, s), 3.21 (3 H, s).

Step B: 1-(4-Fluorophenyl)but-3-en-2-one

To a solution of 220 mL (1.0 M, 220 mmol) of vinylmagnesium bromide in 100 mL THF, was added dropwise under nitrogen atmosphere at 0° C. a solution of 21 g (106.6 mmol) 2-(4-fluorophenyl)-N-methoxy-N-methylacetamide (step A) in ~150 mL dry ether. The reaction mixture was stirred at 0° C. for 0.5 hr then poured slowly into an ice/2N aq HCl mixture. The resulting mixture was diluted with ether and brine, transferred to a separatory funnel and the organic layer separated. The organic layer was washed with brine, dried over drying agent, filtered and the solvent evaporated under vacuum to give 14.2 g of the crude title compound which was used without further purification. $^1$H-NMR (CDCl$_3$): δ: 7.19 (2 H, m), 7.02 (2 H, t, J=9.5 Hz), 6.42 (1 H, dd, J$_1$=14.2 Hz, J$_2$=11 Hz). 6.34 (1 H, d, J=14.2 Hz), 5.86 (1 H, d, J=11 Hz), 3.87 (2 H, s).

Step C: 1E and 1Z tert-butyl{[1-(4-fluorobenzylidene)prop-2-en-1-yl]oxy}dimethylsilane To a solution of 104 mL (104.0 mmol, 1.2 equiv.) of a 1.0M solution of potassium tert-butoxide in THF and 100 mL dry THF under nitrogen atmosphere at −78° C. was added a solution of 14.2 g (86.6 mmol, 1 equiv.) of 1-(4-fluorophenyl)but-3-en-2-one (step B) and 13.0 g (86.6 mmol) tert-butylchlorodimethylsilane in 100 mL dry THF. The reaction mixture was stirred at −78° C. for 6 hr and at RT for 6 hr then quenched by the addition of 50 mL water. The resulting mixture was warmed to RT, diluted with 150 mL hexanes, transferred to a separatory funnel and the organic layer separated. The organic layer was washed with 50 mL brine, dried over anhydrous magnesium sulfate, filtered and the solvent evaporated under vacuum to give 20.5 g of the crude title compounds which were used without further purification. $^1$H-NMR (CDCl$_3$): δ: 7.52 (2 H, m), 6.98 (2 H, m), 6.33 (1 H, dd, J$_1$=13.2 Hz, J$_2$=8.5 Hz), 5.97 (1 H, s), 5.52 (1 H, d, J=13.2 Hz), 5.17 (1 H, d, J=8.5 Hz).

Step D: (3aS,4R,7aR)-2-benzyl-5-{[tert-butyl(dimethyl)silyl]oxy}-4-(4-fluorophenyl)-3a,4,7,7a-tetrahydro-1H-isoindole-1,3(2H)-dione and (3aR,4S,7aS)-2-benzyl-5-{[tert-butyl(dimethyl)silyl]oxy}-4-(4-fluorophenyl)-3a,4,7,7a-tetrahydro-1H-isoindole-1,3(2H)-dione A solution of 15 g (54.0 mmol, 1 equiv.) of 1E and 1Z tert-butyl{[1-(4-fluorobenzylidene)prop-2-en-1-yl]oxy}dimethylsilane (step C) and 12.1 g (64.6 mmol) N-benzylmaleimide in 150 mL dry toluene under nitrogen atmosphere was heated at reflux for 16 hr then cooled to RT. The solvent evaporated under vacuum to give 31 g of the crude title compounds which contained the unreacted N-benzylmaleimide and were used without further purification. $^1$H-NMR (CDCl$_3$): δ: 7.37-7.26 (3 H, m), 7.22 (2 H, m), 7.00 (2 H, m), 6.78 (2 H, t, J=8.5 Hz), 5.07 (1 H, t, J=2.3 Hz), 4.22 (1 H, d, J=16 Hz), 4.15 (1 H, d, J=16 Hz), 3.66 (1 H, d, J=6.5 Hz), 3.52 (1 H, t, J=7.0 Hz), 3.14 (1 H, m), 2.87 (1 H, m), 2.68 (1 H, m), 0.92 (1 H, m), 0.78 (9 H, s), 0.11 (3 H, s), −0.1 (3 H, s).

Step E: (3aS,4S,7aS)-2-benzyl-5-{[tert-butyl(dimethyl)silyl]oxy}-4-(4-fluorophenyl)-2,3,3a,4,7,7a-hexahydro-1H-isoindole and (3aR,4R,7aR)-2-benzyl-5-{[tert-butyl(dimethyl)silyl]oxy}-4-(4-fluorophenyl)-2,3,3a,4,7,7a-hexahydro-1H-isoindole In a round bottom flask was added 7.3 g (192.0 mmol, excess) lithium aluminium hydride in dry ether under nitrogen atmosphere at 0° C. To the resulting mixture was added dropwise a solution of 31 g of the crude intermediate of step D in 100 mL dry methylene chloride under nitrogen atmosphere. The resulting mixture was stirred at RT for 1 hr then carefully quenched at 0° C. by the dropwise addition of 12 mL water, then 10 mL 5.0 N aq. NaOH. The resulting suspension was stirred at RT for 0.5 hr and the solids filtered. The solvent of the filtrate was evaporated under vacuum to give the crude title compounds which were used without further purification.

Step F: (3aS,4S,7aS)-2-benzyl-4-(4-fluorophenyl)octahydro-5H-isoindol-5-one and (3aR,4R,7aR)-2-benzyl-4-(4-fluorophenyl)octahydro-5H-isoindol-5-one To a solution of the intermediate of step E in 60 mL dry acetonitrile under nitrogen atmosphere at RT was added 100 mL (250 mmol) of a 2.5 M solution of HF in acetonitrile. The resulting mixture was stirred at RT for 16 hr then quenched at 0° C. by the dropwise addition of 120 mL 5.0 N aq. NaOH. The acetonitrile was evaporated under vacuum and the resulting aqueous mixture was diluted with ether and water. The resulting mixture was transferred to a separatory funnel and the organic layer separated. The aqueous layer was extracted with an additional portion of ether. The combined organic layers were washed with 50 mL brine, dried over drying agent, filtered and the solvent evaporated under vacuum. The residue was purified by flash column chromatography on silica gel eluting with EtOAc/hexanes (1/1) to give 9.0 g of the racemic title compounds. $^1$H-NMR (CDCl$_3$): δ: 7.27-7.23 (3 H, m), 7.12-7.03 (2 H, m), 3.75 (1 H, d, J=12.9 Hz), 3.61 (2 H, d, J=4.8 Hz), 3.61 (1 H, q, J=14.5 Hz), 2.93 (1 H, t, J=8.5 Hz), 2.68-2.52 (3 H, m), 2.43-2.33 (2 H, m), 2.25 (1 H, m), 2.05 (2 H, m).

Step G: (3aS,4S,5R,7aS)-2-benzyl-4-(4-fluorophenyl)octahydro-1H-isoindol-5-ol and (3aR,4R,5S,7aR)-2-benzyl-4-(4-fluorophenyl)octahydro-1H-isoindol-5-ol To a solution of the intermediate (9.0 g) of step F under nitrogen atmosphere in dry ether at −78° C. was added a 1.0M solution of lithium aluminium hydride (38.3 mL) in ether. The resulting mixture was stirred at −78° C. for 0.5 hr then carefully quenched by the dropwise addition of water, then 5.0 N aq. NaOH. The resulting suspension was stirred at RT for 0.5 hr and the solids filtered. The solvent of the filtrate was evaporated under vacuum to give the crude title compounds as the major compounds which were used without further purification. $^1$H-NMR (CDCl$_3$): δ: 7.38-7.20 (7 H, m), 7.05 (2 H, t, J=8.5 Hz), 3.75 (2 H, s), 3.75 (1 H, m), 2.8-2.65 (4 H, m), 2.60 (1 H, m), 2.50 (1 H, m), 2.38 (1 H, d, J=8.1 Hz), 2.21 (1 H, m), 1.95 (1 H, m), 1.81 (2 H, m), 1.73-1.62 (2 H, m). MS: (MH)$^+$261.9.

Step H: (3aS,4S,5R,7aS)-4-(4-fluorophenyl)octahydro-1H-isoindol-5-ol and (3aR,4R,5S,7aR)-4-(4-fluorophenyl)octahydro-1H-isoindol-5-ol The intermediate of step G was hydrogenated at 50 PSI hydrogen over 10% by weight of 10% Pd—C in ethanol for 16 hr at RT. The catalyst was filtered and the solvent of the filtrate was evaporated under vacuum to give the crude title compounds which were used without further purification.

Step I: tert-Butyl (3aS,4S,5R,7aS)-4-(4-fluorophenyl)-5-hydroxyoctahydro-2H-isoindole-2-carboxylate and tert-butyl (3aR,4R,5S,7aR)-4-(4-fluorophenyl)-5-hydroxy-octahydro-2H-isoindole-2-carboxylate To a solution of 7.5 g (31.9 mmol) of the intermediate of step H in dry methylene chloride under nitrogen atmosphere at RT was added 9.0 g (41.5 mmol) of ditert-butyl dicarbonate. The resulting mixture was stirred at RT for 16 hr then the solvent evaporated under vacuum. The resulting mixture was dissolved in methanol and 5.0 N aq. NaOH was added. The resulting mixture was stirred for 2 hr and the methanol removed under vacuum. The aqueous residue was diluted with EtOAc, transferred to a separatory funnel and the organic layer separated. The aqueous layer was extracted with an additional portion of EtOAc. The combined organic layers were washed with 50 mL brine, dried over magnesium sulfate, filtered and the solvent evaporated under vacuum. The residue was purified by flash column chromatography on silica gel eluting with EtOAc/hexanes (1/4) to give 2.8 g of the racemic title compounds. $^1$H-NMR (CDCl$_3$): δ: $^1$H-NMR (CDCl$_3$): δ $^1$H-NMR (CDCl$_3$): δ 7.22 (2 H, m), 7.07 (2 H, m), 3.73 (1 H, m), 3.48-3.33 (2 H, m), 3.21-3.10 (2 H, m), 2.51 (1 H, m), 2.18 (1 H, t, J=10.7 Hz), 2.25 (1 H, m), 1.98 (1 H, m), 1.97-1.85 (1 H, m), 1.63 (1 H, m), 1.51-1.40 (1 H, m), 1.49, 1.43 (9 H, two singlets). Also isolated was a minor amount of the mixture of cis alcohol (less polar): tert-butyl (3aR,4R,5R,7a R)-4-(4-fluorophenyl)-5-hydroxyoctahydro-2H-isoindole-2-carboxylate and tert-butyl (3aS,4S,5S,7aS)-4-(4-fluorophenyl)-5-hydroxy-octahydro-2H-isoindole-2-carboxylate. $^1$H-NMR (CDCl$_3$): δ: 7.25 (2 H, m), 7.05 (2 H, m), 3.95 (1 H, m), 3.50-3.20 (3 H, m), 3.08, 2.95 (1 H, two doublets, J=14.3 Hz), 2.77 (1 H, m), 2.65-2.55 (2 H, m), 2.15 (1 H, m), 1.82 (2 H, m), 1.58 (1 H, m), 1.45, 1.40 (9 H, two singlets).

Step J: tert-Butyl (3aS,4S,5R,7aS)-5-{[3,5-bis(trifluoromethyl)benzoyl]oxy}-4-(4-fluorophenyl)-octahydro-2H-isoindole-2-carboxylate and tert-butyl (3aR,4R,5S,7aR)-5-{[3,5-bis(trifluoromethyl)benzoyl]oxy}-4-(4-fluorophenyl)octahydro-2H-isoindole-2-carboxylate To a solution of 0.09 g (0.26 mmol) of the intermediate of step I in dry methylene chloride under nitrogen atmosphere at RT was added 0.089 g (0.32 mmol) of 3,5-bis(trifluoromethyl)-benzoyl chloride, 0.07 mL TEA and a catalytic amount of DMAP. The resulting mixture was stirred at RT for 2 hr then transferred to a separatory funnel, washed with sat. aq. NaHCO$_3$, aq. KHSO$_4$, and brine. The combined organic layers dried over magnesium sulfate, filtered and the solvent evaporated under vacuum to afford 0.15 g of the crude title compounds which were used without further purification. $^1$H-NMR (CDCl$_3$): δ: 8.63 (1 H, s), 8.19 (2 H, s), 7.25 (2 H, m), 7.00 (2 H, m), 5.22 (1 H, m), 3.59-3.43 (2 H, m), 3.30-3.20 (2 H, m), 2.83 (1 H, t, J=12.7 Hz), 2.62 (1 H, m), 2.43 (1 H, m), 2.20 (1 H, m), 2.02 (1 H, m), 1.90-1.70 (2 H, m), 1.55, 1.47 (9 H, two singlets).

Step K: tert-Butyl (3aS,4S,7aS)-5-({1-[3,5-bis(trifluoromethyl)phenyl]vinyl}oxy)-4-(4-fluorophenyl)-octahydro-2H-isoindole-2-carboxylate and tert-butyl (3aR,4R,5S,7aR)-5-({1-[3,5-bis(trifluoromethyl)phenyl]vinyl}oxy)-4-(4-fluorophenyl)octahydro-2H-isoindole-2-carboxylate To a solution of 0.15 g (0.26 mmol) of the intermediate of step J in dry THF under nitrogen atmosphere at 0° C. was added 2 mL of a 0.5 M solution of Tebbe reagent in toluene. The resulting mixture was stirred at 0° C. for 0.5 hr then carefully quenched by the dropwise addition of 0.5 mL water, then 0.5 mL of 5.0 N aq. NaOH. The resulting suspension was diluted with ethyl acetate, stirred at RT for 0.5 hr and the solids filtered. The resulting filtrate stirred with 0.5 mL of 5.0 N aq. NaOH for 16 hr and the solids filtered through a pad of filter aid. The solvent was evaporated under vacuum to give the crude title compounds which were used without further purification. $^1$H-NMR (CDCl$_3$): δ: 7.73 (1 H, s), 7.55 (2 H, s), 7.30-7.18 (2 H, m), 7.03 (2 H, m), 4.67 (1 H, s), 4.37 (1 H, s), 4.25 (1 H, m), 3.55-3.30 (3 H, m), 3.27-3.15 (2 H, m), 2.81 (1 H, t, J=12.7 Hz), 2.60 (1 H, m), 2.40-30 (2 H, m), 1.98 (1 H, m), 1.83 (1 H, m), 1.55, 1.47 (9 H, two singlets).

Step L: tert-Butyl (3aS,4S,5R,7aS)-5-{1R-[3,5-bis (trifluoromethyl)phenyl]ethoxy}-4-(4-fluorophenyl) octahydro-2H-isoindole-2-carboxylate and tert-butyl (3aR,4R,5S,7aR)-5-{1S-[3,5-bis(trifluoromethyl) phenyl]ethoxy}-4-(4-fluorophenyl)octahydro-2H-isoindole-2-carboxylate and tert-Butyl (3aS,4S,5R, 7aS)-5-{1S-[3,5-bis(trifluoromethyl)phenyl]-ethoxy}-4-(4-fluorophenyl)octahydro-2H-isoindole-2-carboxylatetert-butyl (3aR,4R,5S,7aR)-5-{1R-[3, 5-bis(trifluoromethyl)phenyl]ethoxy}-4-(4-fluorophenyl)octahydro-2H-isoindole-2-carboxylate The intermediate of step G was hydrogenated at 50 PSI hydrogen over 10% by weight of 10% Pd—C in ethanol for 16 hr at RT. The catalyst was filtered and the solvent of the filtrate was evaporated under vacuum to give the crude title compounds which were purified by prep TLC eluting with EtOAc/hexanes (1/3) to afford the two diastereomers. The less polar (the major) isomer, $^1$H-NMR (CDCl$_3$): δ: 7.73 (1 H, s), 7.58 (2 H, s), 7.25 (2 H, m), 7.10 (2 H, m), 4.05 (1 H, m), 3.23-3.30 (3 H, m), 3.20-3.07 (2 H, m), 2.55 (1 H, t, J=10.3 Hz), 2.45 (1 H, m), 2.33 (1 H, m), 2.20-1.55 (3 H, m), 1.50, 1.43 (9 H, two singlets), 0.95 (3 H, d, J=6.9 Hz), 1.0-0.82 (1 H, m). The minor isomer, $^1$H-NMR (CDCl$_3$): δ 7.70 (1 H, s), 7.20 (2 H, s), 6.95 (2 H, m), 6.87 (2 H, m), 4.45 (1 H, m), 3.40 (1 H, m), 3.27 (1 H, m), 3.15-3.05 (2 H, m), 2.47 (2 H, t, J=11.2 Hz), 2.15 (2 H, m), 1.93 (1 H, m), 1.75 (1 H, m), 1.62 (1 H, m), 1.50 (1 H, m), 1.50, 1.45 (9 H, s), 1.30 (3 H, two doublets, J=6.0 Hz).

Step M: (3aR,4R,5S,7aR)-5-{1(S)-[3,5-bis(Trifluoromethyl)phenyl]ethoxy}-4-(4-fluorophenyl)-octahydro-1H-isoindole and (3aS,4S,5R,7aS)-5-{1(R)-[3,5-bis(Trifluoromethyl)phenyl]-ethoxy}-4-(4-fluorophenyl)octahydro-1H-isoindole The less polar major diastereomer of intermediate Step L was dissolved in dry methylene chloride and treated with anisole and TFA at RT for 2 hr. The solvent was evaporated under vacuum and residue was taken up in EtOAc. The solution was washed with aq. NaOH, then brine, dried over drying agent and filtered. The solvent was evaporated under vacuum to give the crude title compounds. $^1$H-NMR (CDCl$_3$): δ: 7.77 (1 H, s), 7.60 (2 H, s), 7.28 (2 H, m), 7.12 (2 H, t, J=8.2 Hz), 4.07 (1 H, m),3.35 (1 H, m), 3.22-3.10 (2 H, m), 3.00 (1 H, m), 2.85 (1 H, d, J=11.3 Hz), 2.65 (1 H, t, J=11.3 Hz), 2.50 (1 H, m), 2.40 (1 H, m), 1.87-1.68 (2 H, m), 1.53 (1 H, m), 1.30 (1 H, m), 0.95 (3H, d, J=6.0 Hz).

EXAMPLE 2

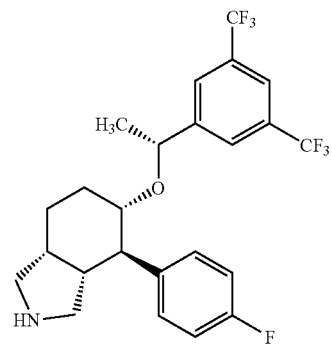

(3aR,4R,5S,7aR)-5-{(1R)-1-[3,5-bis(Trifluoromethyl)phenyl]ethoxy}-4-(4-fluorophenyl)octahydro-1H-isoindole

Step A: (3aS,4S,5R,7aS)-2-Benzyl-4-(4-fluorophenyl)octahydro-1H-isoindol-5-ol and (3aR,4R,5S,7aR)-2-benzyl-4-(4-fluorophenyl)octahydro-1H-isoindol-5-ol Starting with 3.5 g of the racemic mixture of (3aS,4S,5R,7aS)-2-benzyl-4-(4-fluorophenyl)octahydro-1H-isoindol-5-ol and (3aR,4R,5S,7aR)-2-benzyl-4-(4-fluorophenyl)octahydro-1H-isoindol-5-ol (intermediate of Example 1, step G) was separated by chiral HPLC using CHIRACEL AD column eluting with hexanes/EtOH (9/1) to afford the first eluting isomer (3aS,4S,5R,7aS)-2-benzyl-4-(4-fluorophenyl)octahydro-1H-isoindol-5-ol and the second eluting isomer (3aR,4R,5S,7aR)-2-benzyl-4-(4-fluorophenyl)octahydro-1H-isoindol-5-ol.

Step B: tert-Butyl (3aR,4R,5S,7aR)-4-(4-fluorophenyl)-5-hydroxyoctahydro-2H-isoindole-2-carboxylate To a solution of 5.36 g (15.8 mmol) of the second eluting isomer (3aR,4R,5S,7aR)-2-benzyl-4-(4-fluorophenyl)octahydro-1H-isoindol-5-ol (intermediate of step A) in 80 mL EtOH was added 4.31 g (19.7 mmol) of ditert-butyl dicarbonate and 0.5 g of 10% Pd—C. The resulting mixture was hydrogenated at 50 PSI hydrogen for 16 hr at RT. The catalyst was filtered and 5 mL of 5.0 N aq. NaOH was added. The solvent was evaporated under vacuum. The aqueous residue was diluted with EtOAc, transferred to a separatory funnel, washed with brine, dried over drying agent, filtered and the solvent evaporated under vacuum. The residue was purified by flash column chromatography on silica gel eluting with EtOAc/hexanes (1/4) to give the title compound. $^1$H-NMR (CDCl$_3$): δ: 7.22 (2 H, m), 7.07 (2 H, m), 3.73 (1 H, m), 3.48-3.33 (2 H, m), 3.21-3.10 (2 H, m), 2.51 (1 H, m), 2.18 (1 H, t, J=10.7 Hz), 2.25 (1 H, m), 1.98 (1 H, m), 1.97-1.85 (1 H, m), 1.63 (1 H, m), 1.51-1.40 (1 H, m), 1.49, 1.43 (9 H, two singlets).

Step C: tert-Butyl (3aR,4R,5S,7aR)-5-{[3,5-bis(trifluoromethyl)benzoyl]oxy}-4-(4-fluorophenyl)octahydro-2H-isoindole-2-carboxylate To a solution of 4.75 g (14.0 mmol) of the intermediate of step B in dry methylene chloride under nitrogen atmosphere at RT was added 4.71 g (17.0 mmol) of 3,5-bis(trifluoromethyl)benzoyl chloride, 2.4 mL (17.3 mmol) TEA and a catalytic amount of DMAP. The resulting mixture was stirred at RT for 2 hr then transferred to a separatory funnel, washed with saturated. aq. NaHCO$_3$ and brine. The combined organic layers dried over magnesium sulfate, filtered and the solvent evaporated under vacuum to afford the crude title compound which was used without further purification. $^1$H-NMR (CDCl$_3$): δ: 8.63 (1 H, s), 8.19 (2 H, s), 7.25 (2 H, m), 7.00 (2 H, m), 5.22 (1 H, m), 3.59-3.33 (2 H, m), 3.30-3.20 (2 H, m), 2.83 (1 H, t, J=12.7 Hz), 2.62 (1 H, m), 2.43 (1 H, m), 2.20 (1 H, m), 2.02 (1 H, m), 1.90-1.70 (2 H, m), 1.55, 1.47 (9 H, two singlets).

Step D: tert-Butyl (3aR,4R,5S,7aR)-5-({1-[3,5-bis(trifluoromethyl)phenyl]vinyl}oxy)-4-(4-fluorophenyl)octahydro-2H-isoindole-2-carboxylate To a solution 9.5 g (14.0 mmol) of the crude intermediate of step C in dry THF under nitrogen atmosphere at 0° C. was added 66 mL (33 mmol.) of a 0.5 M solution of Tebbe reagent in toluene. The resulting mixture was stirred at 0° C. for 2 hr then carefully quenched by the dropwise addition of 7.5 mL water, then 7.5 mL of 5.0 N aq. NaOH. The resulting suspension was stirred at RT for 0.5 hr and the solids filtered. The resulting filtrate stirred with 5 mL of 5.0 N aq. NaOH for 16 hr and the solids filtered through filter aid. The solvent was evaporated under vacuum and the residue purified by column chromatography eluting with EtOAc/hexanes (1/3) to give the title compound. $^1$H-NMR (CDCl$_3$): δ: 7.73 (1 H, s), 7.55 (2 H, s), 7.30-7.18 (2 H, m), 7.03 (2 H, m), 4.67 (1 H, s), 4.37 (1 H, s), 4.25 (1 H, m), 3.55-3.30 (3 H, m), 3.27-3.15 (2 H, m), 2.81 (1 H, t, J=12.7 Hz), 2.60 (1 H, m), 2.40-30 (2 H, m), 1.98 (1 H, m), 1.83 (1 H, m), 1.55, 1.47 (9 H, two singlets)

Step E: tert-butyl (3aR,4R,5S,7aR)-5-{(1S)-1-[3,5-bis(trifluoromethyl)phenyl]ethoxy}-4-(4-fluorophenyl)octahydro-2H-isoindole-2-carboxylate and tert-butyl (3aR,4R,5S,7aR)-5-{(1R)-1-[3,5-bis(trifluoromethyl)phenyl]ethoxy}-4-(4-fluorophenyl)octahydro-2H-isoindole-2-carboxylate A solution of 10.2 g of the crude intermediate of step D in ethanol was hydrogenated at 50 PSI hydrogen over ~1 g of 10% Pd—C for 3 hr at RT. The catalyst was filtered and the solvent of the filtrate was evaporated under vacuum to give the crude title compounds which were purified by column chromatography eluting with EtOAc/hexanes (2/3) to afford 8.9 g (15.5 mol) the two diastereomers with the major (S) diastereomer. This mixture was taken up in ~150 mL dry THF under nitrogen atmosphere and treated with 80 mL (80 mmol) of a 1.0 M solution of potassium tert-butoxide in THF. The resulting mixture was heated at 40° C. for 1 hr, cooled to RT and quenched by the addition of water. The mixture was diluted with EtOAc, transferred to a separatory funnel, washed with brine, dried over drying agent, filtered and the solvent evaporated under vacuum. The residue was purified by flash column chromatography on silica gel eluting with EtOAc/hexanes (1/3) to give the less polar tert-butyl (3aR,4R,5S,7aR)-5-{(1S)-1-[3,5-bis(trifluoromethyl)phenyl]ethoxy}-4-(4-fluorophenyl)octa-hydro-2H-isoindole-2-carboxylate and the more polar tert-butyl (3aR,4R,5S,7aR)-5-{(1R)-1-[3,5-bis(trifluoromethyl)phenyl]ethoxy}-4-(4-fluorophenyl)octahydro-2H-isoindole-2-carboxylate. $^1$H-NMR (CDCl$_3$): δ: of the less polar isomer: δ: 7.73 (1 H, s), 7.58 (2 H, s), 7.25 (2 H, m), 7.10 (2 H, m), 4.05 (1 H, m), 3.23-3.30 (3 H, m), 3.20-3.07 (2 H, m), 2.55 (1 H, t, J=10.3 Hz), 2.45 (1 H, m), 2.33 (1 H, m), 2.20-1.55 (3 H, m), 1.50, 1.43 (9 H, two singlets), 0.95 (3 H, d, J=6.9 Hz), 1.0-0.82 (1 H, m). $^1$H-NMR (CDCl$_3$) of the more polar isomer: 7.71 (1 H, s), 7.20 (2 H, s), 6.97 (2 H, m), 6.85 (2 H, m), 4.47 (1 H, m), 3.43-3.03 (4 H, m), 2.47 (2 H, m), 2.15 (2 H, m), 1.92 (1 H, t, J=10.5 Hz), 1.80-1.57 (3 H, m), 1.50, 1.43 (9 H, two singlets), 1.30 (3 H, d, J=6.9 Hz).

Step F: (3aR,4R,5S,7aR)-5-{(1R)-1-[3,5-bis(Trifluoromethyl)phenyl]ethoxy}-4-(4-fluorophenyl)octahydro-1H-isoindole hydrochloride salt The more polar diastereomer of intermediate Step E (1.5 g, 2.6 mmol) was dissolved in ~20 mL 4 N HCl in dioxane and stirred at RT for 2 hr. The solvent was evaporated under vacuum and residue was taken up in EtOAc. The solution was washed with aq. NaOH, then brine, dried over drying agent and filtered. The solvent was evaporated under vacuum to give the crude title compound. Treatment with HCL in dioxane affirded the HCl salt $^1$H-NMR (CDCl$_3$): δ: 7.75 (1 H, s), 7.37 (2 H, s), 7.13 (2 H, m), 6.87 (2 H, t, J=8.5 Hz), 4.63 (1 H, q, 6.5 Hz), 3.45 (1 H, td, J$_1$=4 Hz, J$_2$=11.9 Hz), 3.17 (1 H, m), 3.10 (1 H, dd, J$_1$=6.5 Hz, J$_2$=9.5 Hz), 2.90 (1 H, J=12.7 Hz), 2.57 (2 H, m), 2.47 (1 H, t, J=9.5 Hz), 2.25 (1 H, m), 1.98 (2 H, m), 1.68 (1 H, m), 1.10 (3H, d, 6.5 Hz). MS: (MH)$^+$475.9.

EXAMPLE 3

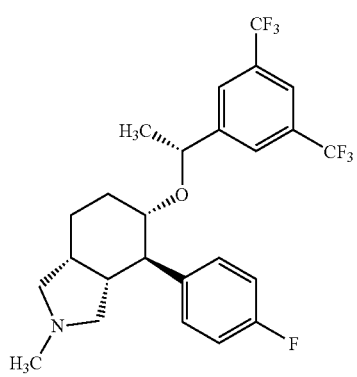

(3aR,4R,5S,7aR)-5-{(1R)-1-[3,5-bis(Trifluoromethyl)phenyl]ethoxy}-4-(4-fluorophneyl)-2-methyl-octahydro-1H-isoindole Step A: (3aR,4R,5S,7aR)-5-{(1R)-1-[3,5-bis(Trifluoromethyl)phenyl]ethoxy}-4-(4-fluorophenyl)-2-methyloctahydro-1H-isoindole To a solution of 30 mg (0.063 mmol) of (3aR,4R,5S,7aR)-5-{(1R)-1-[3,5-bis(trifluoromethyl)phenyl]ethoxy}-4-(4-fluorophenyl)octahydro-1H-isoindole (Example 2) in ~2 mL methanol was added ~20 mg (excess) aq. formaldehyde and 40 mg sodium acetate. The resulting mixture was stirred at RT for 10 min then 20 mg of NaBH$_4$ was added. The resulting mixture was stirred at RT for 1 hr then water was added. The methanol was evaporated under vacuum and residue extracted with ether (2×25 mL). The combined extracts were dried over drying agent, filtered and the solvent was evaporated under vacuum. The residue was purified by prep TLC eluting with EtOAc/MeOH (9/1) to give the title compound. $^1$H-NMR (CDCl$_3$): δ: ppm. 7.68 (1 H, s), 7.23 (2 H, s), 7.02 (2 H, m), 6.87 (2 H, m), 4.45 (1 H, m), 3.27 (1 H,), 2.78-2.65 (2 H, m), 2.57 (2 H, m), 2.45-2.30 (3 H, m), 2.23-2.12 (2 H, m), 1.98 (1 H, m), 1.83-1.68 (2 H, m), 1.30 (3 H, 6.2) MS: (MH)$^+$489.9.

EXAMPLE 4

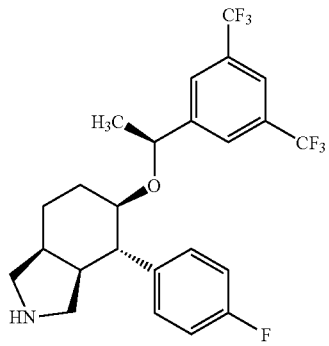

(3aS,4S,5R,7aS)-5-{(1S)-1-[3,5-bis(Trifluoromethyl)phenyl]ethoxy}-4-(4-fluorophenyl)-octahydro-1H-isoindole Step A: tert-Butyl (3aS,4S,5R,7aS)-4-(4-fluorophenyl)-5-hydroxyoctahydro-2H-isoindole-2-carboxylate The title compound was prepared from of (3aS,4S,5R,7aS)-2-benzyl-4-(4-fluorophenyl)octahydro-1H-isoindol-5-ol (the first eluting isomer of Example 2 step A) according to the procedure for Example 2, step B). $^1$H-NMR (CDCl$_3$): δ: 7.22 (2 H, m), 7.07 (2 H, m), 3.73 (1 H, m), 3.48-3.33 (2 H, m), 3.21-3.10 (2 H, m), 2.51 (1 H, m), 2.18 (1 H, t, J=10.7 Hz), 2.25 (1 H, m), 1.98 (1 H, m), 1.97-1.85 (1 H, m), 1.63 (1 H, m), 1.51-1.40 (1 H, m), 1.49, 1,43 (9 H, two singlets).

Step B: tert-Butyl (3aS,4S,5R,7aS)-5-{[3,5-bis(trifluoromethyl)benzoyl]oxy}-4-(4-fluorophenyl)octahydro-2H-isoindole-2-carboxylate The title compound was prepared from the intermediate of step A according to the procedure for Example 2, step C. $^1$H-NMR (CDCl$_3$): δ: 8.63 (1 H, s), 8.19 (2 H, s), 7.25 (2 H, m), 7.00 (2 H, m), 5.22 (1 H, m), 3.59-3.433 (2 H, m), 30-3.20 (2 H, m), 2.83 (1 H, t, J=12.7 Hz), 2.62 (1 H, m), 2.43 (1 H, m), 2.20 (1 H, m), 2.02 (1 H, m), 1.90-1.70 (2 H, m), 1.55, 1.47 (9 H, two singlets).

Step C: tert-Butyl (3aS,4S,5R,7aS)-5-({1-[3,5-bis(trifluoromethyl)phenyl]vinyl}oxy)-4-(4-fluorophenyl)octahydro-2H-isoindole-2-carboxylate The title compound was prepared from the intermediate of step B according to the procedure for Example 2, step D. $^1$H-NMR (CDCl$_3$): δ 7.73 (1 H, s), 7.55 (2 H, s), 7.30-7.18 (2 H,m), 7.03 (2 H, m), 4.67 (1 H, s), 4.37 (1 H, s), 4.25 (1 H, m), 3.55-3.30 (3 H, m), 3.27-3.15 (2 H, m), 2.81 (1 H, t, J=12.7 Hz), 2.60 (1 H, m), 2.40-2.30 (2 H, m), 1.98 (1 H, m), 1.83 (1 H, m), 1.55, 1.47 (9 H, two singlets).

Step D: tert-Butyl (3aS,4S,5R,7aS)-5-{(1S)-1-[3,5-bis(trifluoromethyl)phenyl]ethoxy}-4-(4-fluorophenyl)octahydro-2H-isoindole-2-carboxylate and tert-butyl (3aS,4S,5R,7aS)-5-{(1R)-1-[3,5-bis(trifluoromethyl)phenyl]ethoxy}-4-(4-fluorophenyl)octahydro-2H-isoindole-2-carboxylate The title compounds were prepared from the intermediate of step C according to the procedure for Example 2, step E.

¹H-NMR (CDCl₃): δ: the less polar isomer, δ: 7.73 (1 H, s), 7.58 (2 H, s), 7.25 (2 H, m), 7.10 (2 H, m), 4.05 (1 H, m), 3.23-3.30 (3 H, m), 3.20-3.07 (2 H, m), 2.55 (1 H, t, J=10.3 Hz), 2.45 (1 H, m), 2.33 (1 H, m), 2.20-1.55 (3 H, m), 1.50, 1.43 (9 H, two singlets), 0.95 (3 H, d, J=6.9 Hz), 1.0-0.82 (1 H, m). ¹H-NMR (CDCl₃) of the more polar isomer: 7.71 (1 H, s), 7.20 (2 H, s), 6.97 (2 H, m), 6.85 (2 H, m), 4.47 (1 H, m), 3.43-3.03 (4 H, m), 2.47 (2 H, m), 2.15 (2 H, m), 1.92 (1 H, t, J=10.5 Hz), 1.80-1.57 (3 H, m), 1.50, 1.43 (9 H, two singlets), 1.30 (3 H, d, J=6.9 Hz).

Step E: (3aS,4S,5R,7aS)-5-{(1S)-1-[3,5-bis(Trifluoromethyl)phenyl]ethoxy}-4-(4-fluorophenyl)octahydro-1H-isoindole The title compound was prepared from of tert-butyl (3aS,4S,5R,7aS)-5-{(1S)-1-[3,5-bis(trifluoromethyl)phenyl]ethoxy}-4-(4-fluorophenyl)octahydro-2H-isoindole-2-carboxylate (step D) according to the procedure for Example 2, step F. The more polar isomer, ¹H-NMR (CDCl₃): δ: 7.68 (1 H, s), 7.20 (2 H, s), 7.05 (2 H, m), 6.87 (2 H, t, J=8.2 Hz), 4.27 (1 H, m), 3.28 (1 H, m),3.20-3.05 (2 H, m), 2.88 (1 H, m), 2.72 (1 H, d, J=11.7 Hz), 2.58 (1 H, t, J=11.9 Hz), 2.40 (1 H, m), 2.20 (1 H, m), 2.10 (1 H, m), 1.92 (1 H, m), 1.83 (1 H, m), 1.60 (1 H, m), 1.30 (3 H, d, J=6.0 Hz). MS: (MH)⁺ 475.9.

EXAMPLE 5

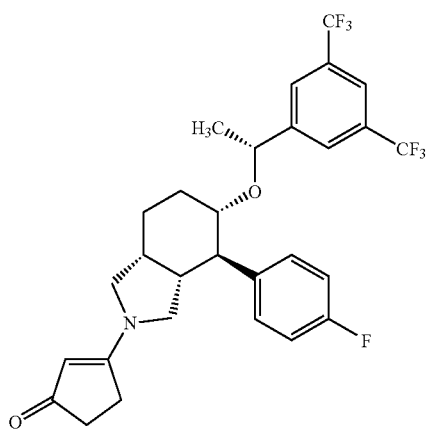

3-[(3aR,4R,5S,7aR)-5-{(1R)-1-[3,5-bis(Trifluoromethyl)phenyl]ethoxy}-4-(4-fluorophenyl)-octahydro-2H-isoindol-2-yl]cyclopent-2-en-1-one To a solution of 12.3 mg (0.26 mmol) of (3aR,4R,5S,7aR)-5-{(1R)-1-[3,5-bis(trifluoromethyl)phenyl]ethoxy}4-(4-fluorophenyl)octahydro-1H-isoindole (Example 2) in ~2 mL dry toluene was added 2.7 mg (0.028 mmol) cyclopentane-1,3-dione and a catalytic amount (~0.5 mg) of PTSA. The resulting mixture was heated at reflux for 16 hr. The solvent was removed vacuum and the residue was purified by prep TLC eluting with EtOAc/MeOH (95/5) to afford the title compound. ¹H-NMR (CDCl₃): δ: 7.73 (1 H, s), 7.20 (2 H, s), 7.03-6.90 (2 H, m), 4.98, 4.80 (1 H, s), 4.50 (1 H, m), 3.62-3.18 (2 H, m), 3.30-3.18 (3 H, m), 3.15, 2.97 (1 H, d, J=11.2 Hz), 2.68 (2 H, m), 2.55-2.40 (4 H, m), 2.17 (1 H, m), 2.20 (1 H, m), 2.00 (1 H, m), 1.85 (1 H, m), 1.62 (1 H, m), 1.33 (3 H, d, J=6.2 Hz). MS: (MH)⁺ 556.0.

EXAMPLE 6

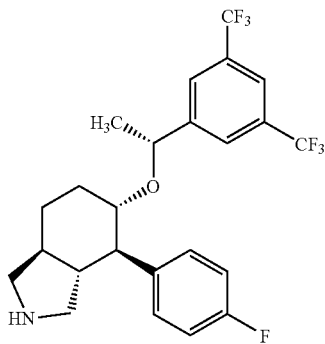

(3aR,4R,5S,7aS)-5-{(1R)-1-[3,5-bis(Trifluoromethyl)phenyl]ethoxy}-4-(4-fluorophenyl)-octahydro-1H-isoindole Step A: Diethyl 4-{[tert-butyl(dimethyl)silyl]oxy}-3-(4-fluorophenyl)cyclohex-4-ene-1,2-dicarboxylate To a solution of 37 g (~80% pure, 133.1 mmol, 1 equiv.) of 1E and 1Z-tert-butyl{[1-(4-fluorobenzylidene)prop-2-en-1-yl]oxy}dimethylsilane (Example 1, step C) and 17 mL (18 g, 104.6 mmol) diethyl(2E)-but-2-enedioate in 200 mL xylenes under nitrogen atmosphere was heated at 160° C. for 5 hr then cooled to RT. The solvent was evaporated under vacuum to give an oil which was used without further purification.

Step B: Racemic Diethyl(1S,2S,3R)-3-(4-fluorophenyl)-4-oxocyclohexane-1,2-dicarboxylate and diethyl(1R,2R,3S)-3-(4-fluorophenyl)-4-oxocyclohexane-1,2-dicarboxylate To a solution of the above intermediate in 30 mL acetonitrile under nitrogen atmosphere at RT in a plastic reaction flask was added 200 mL (500 mmol) of a 2.5 M solution of HF in acetonitrile. The resulting mixture was stirred at RT for 24 hr. The reaction mixture was added to a mixture of 125 mL 5.0 N aq. NaOH and 100 g ice, then stirred at RT for 5 min. The resulting mixture was diluted with 300 mL ether. The resulting mixture was transferred to a separatory funnel and the organic layer separated. The aqueous layer was saturated with NaCl then extracted with an additional portion of ether. The combined organic layer was washed with brine, dried over drying agent, filtered and the solvent evaporated under vacuum to give 40.8 g of the title compounds. ¹H-NMR (CDCl₃): δ: 7.10 (2 H, m), 7.05 (2 H, m), 4.23-4.15 (2 H, m), 3.90-3.80 (3 H, m), 3.32 (1 H, td, J₁=13.0 Hz, J₂=4.0 Hz), 3.21 (1 H, t, J=12.9 Hz), 2.68 (2 H, m), 2.55 (1 H, m), 2.07 (1 H, m), 1.30 (1 H, t, J=7.2 Hz), 0.85 (3 H, t, J=7.2 Hz).

Step C: Racemic diethyl(1S,2S,3R,4S)-3-(4-fluorophenyl)-4-hydroxycyclohexane-1,2-dicarboxylate and diethyl(1R,2R,3S,4R)-3-(4-fluorophenyl)-4-hydroxycyclohexane-1,2-dicarboxylate To a solution 40.2 g (119.3 mmol) of the intermediate of step B in 150 mL ethanol under nitrogen atmosphere at −78° C. was added 4.1 g (108.5 mmol) NaBH₄ powder. The resulting mixture was stirred at −78° C. for 0.5 hr then at RT for 2 hr. The reaction mixture was carefully quenched by the addition of 30 mL water and carefully acidified with 2N aq. HCl. The solvent was evaporated under vacuum. The residue dissolved in ether, transferred to a separatory funnel, washed with sat. aq. NaHCO$_3$ and brine, dried over drying agent, filtered and the solvent evaporated under vacuum to give the crude title compounds which were purified in the next step. $^1$H-NMR (CDCl$_3$): δ: 7.25 (2 H, m), 7.05 (2 H, t, J=8.2 Hz), 4.20-4.05 (2 H, m), 3.85-3.72 (3 H, m), 2.85 (2 H, m), 2.70 (1 H, t, J=7.8 Hz), 2.25 (2 H, m), 1.70 (1 H, m), 1.60 (1 H, m), 1.25 (3 H, t, J=7.2 Hz), 0.85 (3 H, t, J=7.2 Hz).

Step D: Diethyl(1S,2S,3R,4S)-3-(4-fluorophenyl)-4-hydroxycyclohexane-1,2-dicarboxylate Starting with 21 g of the racemic mixture of diethyl(1S,2S,3R,4S)-3-(4-fluorophenyl)-4-hydroxycyclohexane-1,2-dicarboxylate and diethyl(1R,2R,3S,4R)-3-(4-fluorophenyl)-4-hydroxycyclohexane-1,2-dicarboxylate (step C) was separated by preparative chiral HPLC using CHIRACEL AD column eluting with heptanes/i-PrOH (9/1) to afford 9.09 g of the desired first eluting isomer diethyl(1S,2S,3R,4S)-3-(4-fluorophenyl)-4-hydroxycyclohexane-1,2-dicarboxylate.

Step E: (1S)-1-[3,5-bis(trifluoromethyl)phenyl]ethyl-2,2,2-trichloroethanimidoate A solution of 25.82 g (100 mmol) of (1S)-1-[3,5-bis(trifluoromethyl)phenyl]ethanol in 200 mL dry diethyl ether under nitrogen atmosphere was cooled in an ice/water bath. Neat 3 mL (20 mmol, 0.2 equiv) DBU was added to the reaction flask then the mixture was stirred at 0° C. for ten min. Slowly 15 mL (150 mmol, 1.5 equiv.) trichloroacetonitrile was added dropwise over 15 min. The reaction was stirred at 0° C. for 2 hr. during which time it became deep yellow in color. The volatiles were removed under vacuum using a cool bath (<35° C.) to give a pale brown mobile liquid which was purified by column chromatography on silica gel (3"×10" pad) in two batches eluting with hexanes/EtOAc (9/1) then hexanes/EtOAc (4/1). The product fractions were combined and the solvent removed under vacuum to give 37.5 g of the title compound as a pale yellow oil. $^1$H-NMR (CDCl$_3$): δ: 1.74 (3 H, d, J=6.5 Hz), 6.07 (1 H, q, J=6.5 Hz), 7.82 (1 H, s), 7.86 (2 H, s), 8.40 (1 H, br. s) ppm.

Step F: Diethyl(1S,2S,3R,4S)-4-{(1R)-1-[3,5-bis(trifluoromethyl)phenyl]ethoxy}-3-(4-fluorophenyl)cyclohexane-1,2-dicarboxylate To a solution of 9.09 g (26.9 mmol) of the first eluting isomer diethyl(1S,2S,3R,4S)-3-(4-fluorophenyl)-4-hydroxycyclohexane-1,2-dicarboxylate (step D) and 21.5 g (53.5 mmol) of (1S)-1-[3,5-bis(trifluoromethyl)phenyl]ethyl-2,2,2-trichloroethanimidoate (step E) in 250 mL of cyclohexane/1,2-chloroethane (3/1) under nitrogen atmosphere at −5° C. was added 0.51 mL (3.58 mmol) of 54% HBF$_4$ in ether. The reaction mixture was stirred at −5° C. to at 0° C. for 2 hr then diluted with ether. The mixture was washed with sat. aq. NaHCO$_3$. The organic layer was dried over drying agent, filtered and the solvent evaporated under vacuum. The residue was purified by flash column chromatography on silica gel eluting with EtOAc/hexanes (1/4) to give 9.2 g of the title compound as an oil. $^1$H-NMR (CDCl$_3$): δ: δ: 7.70 (1 H, s), 7.20 (2 H, s), 7.00 (2 H, m), 6.85 (2 H, t, J=8.5 Hz), 4.43 (1 H, q, J=6.0 Hz), 4.20-4.10 (2 H, m), 3.80-3.73 (2 H, m), 3.36 (1 H, m), 2.90-2.76 (2 H, m), 2.40 (1 H, m), 2.28 (1 H, m), 1.63-1.55 (2 H, m), 1.33 (3 H, d, J=6.0 Hz), 1.25 (3 H, t, J=7.2 Hz), 0.82 (3 H, t, J=7.2 Hz). Unreacted starting alcohol could be recovered by flushing the column with EtOAc and reused in the above reaction.

Step G: [(1S,2R,3R,4S)-4-{(1R)-1-[3,5-bis(Trifluoromethyl)phenyl]ethoxy}-3-(4-fluorophenyl)cyclohexane-1,2-diyl]dimethanol To a solution of 9.2 g (15.9 mmol) diethyl(1S,2S,3R,4S)-4-{(1R)-1-[3,5-bis(trifluoromethyl)phenyl]ethoxy}-3-(4-fluorophenyl)cyclohexane-1,2-dicarboxylate (step F) in 100 mL THF under nitrogen atmosphere at RT was added 2 g (112.4 mmol, excess) LiBH$_4$ powder. The resulting mixture was heated at 68° C. for 2 hr then cooled to RT. The reaction mixture was carefully quenched by the addition of 30 mL water, then extracted with EtOAc. The combined organic extracts were dried over drying agent, filtered and the solvent evaporated under vacuum to give 7.5 g of the crude title compound as an oil which was used without further purification. $^1$H-NMR (CDCl$_3$): δ: 7.70 (1 H, s), 7.20 (2 H, s), 7.00 (2 H, m), 6.87 (2 H, t, J=8.2 Hz), 4.20 (1 H, q, J=6.0 Hz), 3.78 (1 H, m), 3.67 (1 H, m), 3.52 (1 H, m), 3.30-3.20 (2 H, m), 2.58 (1 H, t, J=11.9 Hz), 2.32 (1 H, m), 1.87 (1 H, m), 1.87 (1 H, m), 1.65 (1 H, m), 1.58-1.35 (3 H, m), 1.30 (3 H, t, J=6.0 Hz).

Step H: [(1S,2R,3R,4S)-4-{(1R)-1-[3,5-bis(Trifluoromethyl)phenyl]ethoxy}-3-(4-fluorophenyl)cyclohexane-1,2-diyl]di(methylene)dimethanesulfonate To a solution of 1.82 g (3.7 mmol) [(1S,2R,3R,4S)-4-{(1R)-1-[3,5-bis(trifluoromethyl)phenyl]ethoxy}-3-(4-fluorophenyl)cyclohexane-1,2-diyl]dimethanol (step G) in 50 mL methylene chloride cooled to −5° C. in an ice/salt bath was added 1.0 mL (3.5 equiv.) methane-sulfonyl chloride; 2.1 mL (4 equiv.) TEA and 44 mg (0.1 equiv.) DMAP. The reaction mixture was stirred at −5° C. for 30 min then quenched at that temperature by the addition of 20 mL sat. aq. NaHCO$_3$. The mixture was warmed to RT. The organic layer was separated and the aqueous layer extracted with additional 50 mL methylene chloride. The combined organic layer was washed with 20 mL 2N aq. HCl, 30 mL sat. aq. NaHCO$_3$, brine, dried over MgSO$_4$ drying agent, filtered and the solvent evaporated under vacuum to give the title compound as an oil which was used without further purification.

Step I: (3aR,4R,5S,7aS)-2-Benzyl-5-{(1R)-1-[3,5-bis(trifluoromethyl)phenyl]ethoxy}-4-(4-fluorophenyl)octahydro-1H-isoindole In a pressure tube was placed a solution of crude [(1S,2R,3R,4S)-4-{(1R)-1-[3,5-bis(trifluoromethyl)phenyl]ethoxy}-3-(4-fluorophenyl)cyclohexane-1,2-diyl]di(methylene) dimethanesulfonate (step H) in ~20 mL ethanol and 1.2 mL (~3 equiv.) benzylamine. The pressure tube was sealed and heated at 150° C. in an oil bath for 3 hr. The tube was cooled to RT and opened. The resulting mixture was transferred to a round bottom flask and the solvent removed under vacuum. The residue was diluted with 100 mL EtOAc, washed with 20 mL 5N aq. NaOH, dried over MgSO$_4$ drying agent, filtered and the solvent was evaporated under vacuum. The residue was purified by flash column chromatography on silica gel eluting with EtOAc to give 1.6 g of the title compound. $^1$H-NMR (CDCl$_3$): δ: 7.35-7.20 (5 H, m), 7.50 (2 H, s), 6.97 (2 H, m), 6.85 (2 H, t, J=8.2 Hz), 4.42 (1 H, t, J=6.0 Hz), 3.75 (2 H, d, J=13.4 Hz), 3.50 (2 H, d, J=13.4 Hz), 3.30 (1 H, m), 2.96 (1 H, m), 2.52 (3 H, m), 2.19 (2 H, m), 1.98 (1 H, m), 1.97 (1 H, m), 1.86 (2 H, m), 1.57 (1 H, m), 1.33 (3 H, t, J=6.0 Hz), 1.30 (1 H, m). MS: (MH)$^+$ 566.0.

Step J: (3aR,4R,5S,7aS)-5-{(1R)-1-[3,5-bis(Trifluoromethyl)phenyl]ethoxy}-4-(4-fluorophenyl)octahydro-1H-isoindole To a solution of (3aR,4R,5S,7aS)-2-benzyl-5-{(1R)-1-[3,5-bis(trifluoromethyl)phenyl]ethoxy}-4-(4-fluorophenyl)octahydro-1H-isoindole (step H) in ~50 mL EtOH was added 0.2 g (20% by weight) of 10% Pd(OH)$_2$—C. The reaction mixture was hydrogenated at 50 PSI for 16 hr at RT. The catalyst was filtered and the solvent of the filtrate was evaporated under vacuum to give the title compound. $^1$H-NMR (CDCl$_3$): δ: 7.70 (1 H, s), 7.20 (2 H, s), 6.95 (2 H, m), 6.87 (2 H, t, J=8.5 Hz), 4.42 (1 H, q, J=6.5 Hz), 3.55 (1 H, m), 3.30 (1 H, m), 3.10-2.95 (2 H, m), 2.83 (1 H, m), 2.70 (1 H, m), 2.52 (1 H, m), 2.40 (1 H, m), 2.10 (1 H, m), 1.97 (2 H, m), 1.80 (1 H, m), 1.33 (3 H, d, J=6.2 Hz). MS: (MH)$^+$ 476.1.

EXAMPLE 7

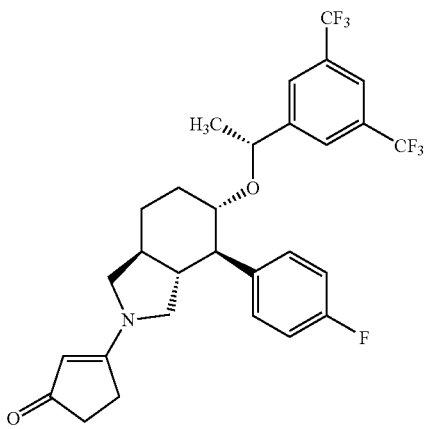

3-[(3aR,4R,5S,7aS)-5-{(1R)-1-[3,5-bis(Trifluoromethyl)phenyl]ethoxy}-4-(4-fluorophenyl)-octahydro-2H-isoindol-2-yl]cyclopent-2-en-1-one To a solution of 0.73 g (1.5 mmol) of (3aR,4R,5S,7aS)-5-{(1R)-1-[3,5-bis(trifluoromethyl)phenyl]ethoxy}-4-(4-fluorophenyl)octahydro-1H-isoindole (Example 6) in ~25 mL dry toluene was added 0.166 g (1.7 mmol) cyclopentane-1,3-dione and 0.03 g (0.15 mmol) of PTSA. The resulting mixture was heated at reflux for 2 hr. The solvent was removed under vacuum and the residue was purified by prep TLC eluting with CHCl$_3$/2N NH$_3$ in MeOH (9/1) to afford 0.49 g the title compound. The compound could be further purified by chiral HLPC on CHIRACEL AD column eluting with hexanes/EtOH (9/1). The compound could be crystallized (mp=216.5-217.5° C.) from hexanes/EtOAc or hexanes/EtOH. $^1$H-NMR (CDCl$_3$): δ: 7.71 (1 H, s), 7.23 (2 H, s), 7.00 (2H, m), 6.93 (2 H, t, J=8.2 Hz), 4.89, 4.48 (1 H, s), 4.47 (1 H, m), 3.71, 3.48 (1 H, m), 3.35 (1 H, m), 3.28-3.17 (1 H, m), 2.95 (1 H, m), 2.95, 2.81 (1 H, m), 2.68 (2 H, m), 2.45 (2 H, m), 2.37 (2 H, m), 2.15 (1 H, m), 1.93 (2 H, m), 1.60 (1 H, m), 1.38 (1 H, m), 1.36 (3 H, t, J=6.0 Hz). MS: (MH)$^+$ 556.0.

EXAMPLE 8

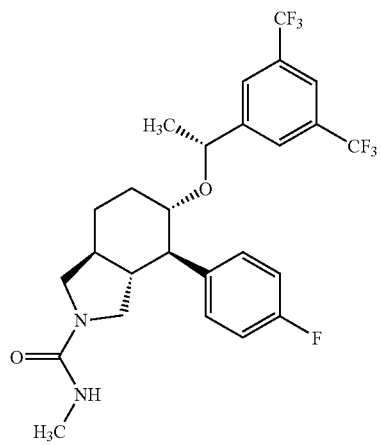

(3aR,4R,5S,7aS)-5-{(1R)-1-[3,5-bis(Trifluoromethyl)phenyl]ethoxy}-4-(4-fluorophenyl)-N-methyloctahydro-2H-isoindole-2-carboxamide To a solution of ~20 mg (0.042 mmol) of (3aR,4R,5S,7aS)-5-{(1R)-1-[3,5-bis(Trifluoromethyl)phenyl]ethoxy}-4-(4-fluorophenyl)octahydro-1H-isoindole (Example 6) in ~2 mL dry methylene chloride at RT was added several drops of methylisocyanate. The resulting mixture was stirred at RT 2 hr. Several drops of 2 N aq. NaOH were added to the reaction mixture. The organic layer was separated, dried over drying agent, filtered and the solvent removed under vacuum. The residue was purified by pre TLC eluting with EtOAc and the major product band isolated. The residue was taken up in EtOAc and the solids filtered. The solvent of the filtrate was removed under vacuum to afford the title compound. $^1$H-NMR (CDCl$_3$): δ: 7.71 (1 H, s), 7.23 (2 H, s), 6.98 (2 H, m), 6.85 (2 H, m), 4.45 (1 H, m), 4.00 (1 H, m), 3.68 (1 H, m), 3.36 (1 H, m), 3.08 (1 H, m), 2.93 (1 H, m), 2.77 (1 H, m), 2.55 (1 H, m), 2.45 (1 H, m), 2.10 (1 H, d, J=12.5 Hz), 2.00-1.70 (2 H, m), 1.70-1.50 (1 H, m), 1.30 (1 H, m), 1.30 (3 H, d, J=6.0 Hz). MS: (MH)$^+$ 533.5.

EXAMPLE 9

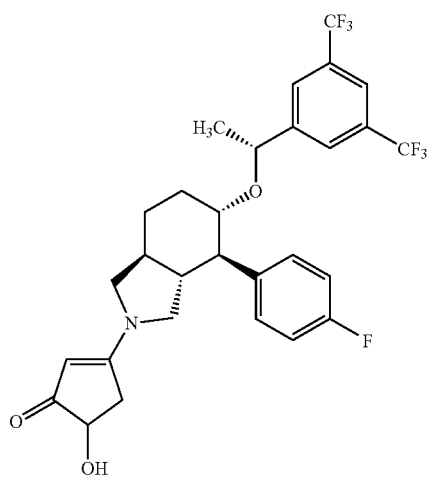

3-[(3aR,4R,5S,7aS)-5-{(1R)-1-[3,5-bis(Trifluoromethyl)phenyl]ethoxy}-4-(4-fluorophenyl)-octahydro-2H-isoindol-2-yl]-5-hydroxycyclopent-2-en-1-one To a solution of 20 mg (0.07 mmol) of 3-[(3aR,4R,5S,7aS)-5-{(1R)-1-[3,5-bis(trifluoromethyl)phenyl]ethoxy}-4-(4-fluorophenyl)octahydro-2H-isoindol-2-yl]cyclopent-2-en-1-one (Example 7) and 170 mg (0.39 mmol) MoOPH in ~2 mL dry THF under nitrogen atmosphere at −78° C. was added ×0.076 mL (0.15 mmol) of 2.0 M solution of KHMDS. The resulting mixture was stirred at −78° C. for 2 hr then quenched by the addition of sat. aq. $NH_4Cl$. The mixture was extracted with EtOAc. The combined organic extracts were washed with brine, dried over drying agent and filtered. The residue was purified by prep TLC eluting with $CHCl_3/2N\ NH_3$ in MeOH (9/1) to afford the title compound as a mixture of diastereomers. $^1$H-NMR ($CDCl_3$): δ: 7.71 (1 H, s), 7.23 (2 H, s), 7.00 (2 H, m), 6.93 (2 H, t, J=8.2 Hz), 4.85, 4.71 (1 H, s), 4.47 (1 H, m), 4.20 (1 H, m), 3.80-3.65 (1 H, m), 3.37 (1 H, m), 3.25-3.08 (1 H, m), 3.10-2.80 (3 H, m), 2.58 (1 H, m), 2.50-2.30 (1 H, m), 2.15 (1 H, m), 1.95 (2 H, m), 1.35 (3 H, d, J=6.0 Hz). MS: (MH)$^+$ 572.5. The diastereomers were separated by HPLC on CHIRACEL AS column eluting with hexanes/EtOH (85/15) to afford the individual diastereomers.

EXAMPLE 10

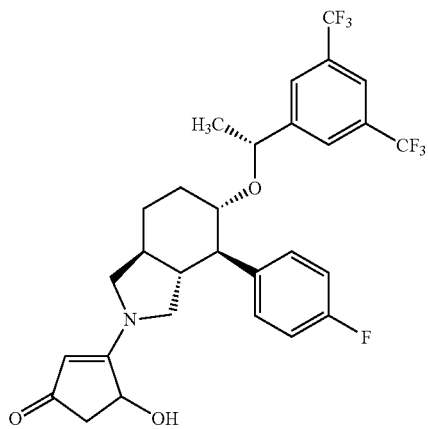

3-[(3aR,4R,5S,7aS)-5-{(1R)-1-[3,5-bis(Trifluoromethyl)phenyl]ethoxy}-4-(4-fluorophenyl)-octahydro-2H-isoindol-2-yl]-4-hydroxycyclopent-2-en-1-one Step A: 4-[(3aR,4R,5S,7aS)-5-{(1R)-1-[3,5-bis(trifluoromethyl)phenyl]ethoxy}-4-(4-fluorophenyl)octahydro-2H-isoindol-2-yl]cyclopent-4-ene-1,3-dione The title compound was prepared from (3aR,4R,5S,7aS)-5-{(1R)-1-[3,5-bis(trifluoromethyl)phenyl]ethoxy}-4-(4-fluorophenyl)octahydro-1H-isoindole (Example 6) and cyclopentane-1,2,4-trione according to the procedure of Example 7. MS: (MH)$^+$ 570.0

Step B: 3-[(3aR,4R,5S,7aS)-5-{(1R)-1-[3,5-bis(Trifluoromethyl)phenyl]ethoxy}-4-(4-fluorophenyl)-octahydro-2H-isoindol-2-yl]-4-hydroxycyclopent-2-en-1-one The title compound was prepared as a mixture of diastereomers from the intermediate of step A according to the procedure of Example 6, step C (NaBH4 in methanol). $^1$H-NMR ($CDCl_3$): rotamers; δ: 7.71 (1 H, s), 7.23 (2 H, s), 7.00 (2 H, m), 6.93 (2 H, t, J=8.2 Hz), 4.88-4.65 (2 H, m), 4.46 (1 H, m), 4.07 (0.5 H, m), 3.83 (0.5 H, m), 3.55 (1 H, m), 3.35 (1 H, m), 3.28 (1 H, m), 2.97 (2 H, m), 2.92 (1 H, m), 2.58 (1 H, m), 2.43 (1 H, m), 2.25 (1 H, m), 2.13 (1 H, m), 2.05-1.85 (2 H, m), 1.70-1.55 (2 H, m), 1.30 (3 H, 2d, J=6.0 Hz). MS: (MH)$^+$ 572.5 The diastereomers were separated by HPLC on CHIRACEL OD column eluting with hexanes/EtOH (85/15) to afford the individual diastereomers.

EXAMPLE 11

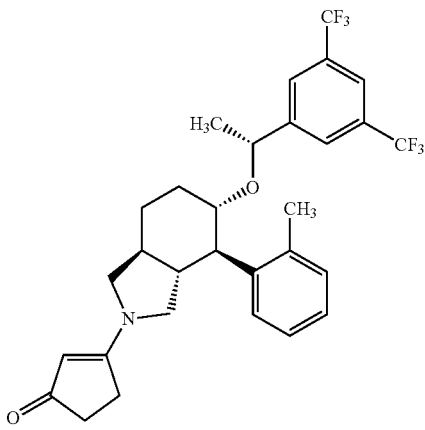

3-[(3aR,4R,5S,7aS)-5-{(1R)-1-[3,5-bis(Trifluoromethyl)phenyl]ethoxy}-4-(2-methylphenyl)-octahydro-2H-isoindol-2-yl]cyclopent-2-en-1-one Step A: 2-(2-Methylphenyl)-N-methoxy-N-methylacetamide The title compound was prepared from 2-(methylphenyl) acetic acid according to the procedure for Example 1, Step A. $^1$H-NMR ($CDCl_3$): δ: 7.23 (4 H, m), 3.83 (2 H, s), 3.65 (3 H, s), 3.28 (3 H, s), 2.36 (3 H, s).

Step B: 1-(2-Methylphenyl)but-3-en-2-one

The title compound was prepared from the intermediate of step A according the procedure of Example 1, step B. $^1$H-NMR ($CDCl_3$): δ: 7.24-7.11 (4 H, m), 6.42 (1 H, dd, $J_1$=14.2 Hz, $J_2$=11 Hz), 6.34 (1 H, d, J=14.2 Hz), 5.81 (1 H, d, J=11 Hz), 3.90 (2 H, s) 2.26 (3 H, s).

Step C: 1E and 1Z tert-butyl{[1-(2-Methylbenzylidene)prop-2-en-1-yl]oxy}dimethylsilane The title compound was prepared from the intermediate of step B according to the procedure of Example 1, step C. $^1$H-NMR ($CDCl_3$): δ: 7.22-7.07 (4 H, m), 6.40 (1 H, dd, $J_1$=13.2 Hz, $J_2$=8.5 Hz), 5.85 (1 H, s), 5.54 (1 H, d, J=13.2 Hz), 5.19 (1 H, d, J=8.5 Hz) 2.28 (3 H, s).

Step D: Diethyl 4-{[tert-butyl(dimethyl)silyl]oxy}-3-(2-methylphenyl)cyclohex-4-ene-1,2-dicarboxylate The title compound was prepared from the intermediate of step C according to the procedure of Example 6, step A and was used without further purification.

Step E: Racemic diethyl(1S,2S,3R)-3-(2-methylphenyl)-4-oxocyclohexane-1,2-dicarboxylate and diethyl(1R,2R,3S)-3-(2-methylphenyl)-4-oxocyclohexane-1,2-dicarboxylate The title compounds were prepared from the intermediate of step D according to the procedure of Example 6, step B. $^1$H-NMR (CDCl$_3$): δ: 7.26-7.09 (4 H, m), 4.23-4.12 (2 H, m), 3.90-3.80 (3 H, m), 3.32 (1 H, td, J$_1$=13.0 Hz, J$_2$=4.0 Hz), 3.28 (1 H, t, J=13 Hz), 2.67 (2 H, m), 2.50 (1 H, m), 2.24 (3 H, s), 2.09 (1 H, m), 1.25 (3 H, t, J=7.2 Hz), 0.83 (3 H, t, J=7.2 Hz).

Step F: Racemic diethyl(1S,2S,3R,4S)-3-(2-methylphenyl)-4-hydroxycyclohexane-1,2-dicarboxylate and diethyl(1R,2R,3S,4R)-3-(2-methylphenyl)-4-hydroxycyclohexane-1,2-dicarboxylate The title compounds were prepared from the intermediate of step E according to the procedure of Example 6, step C. $^1$H-NMR (CDCl$_3$): δ: 7.20-7.10 (4 H, m), 4.15-4.07 (2 H, m), 3.88-3.66 (3 H, m), 3.09 (1 H, t), 2.83 (2 H, m), 2.30 (3 H, s), 2.24-2.15 (2 H, m), 1.68 (1 H, m), 1.57 (1 H, m), 1.25 (3 H, t, J=7.2 Hz), 0.83 (3 H, t, J=7.2 Hz),

Step G: Diethyl(1S,2S,3R,4S)-3-(2-methylphenyl)-4-hydroxycyclohexane-1,2-dicarboxylate The racemic mixture of diethyl(1S,2S,3R,4S)-3-(2-methylphenyl)-4-hydroxycyclohexane-1,2-dicarboxylate and diethyl(1R,2R,3S,4R)-3-(2-methylphenyl)-4-hydroxycyclohexane-1,2-dicarboxylate (step F) was separated by preparative chiral HPLC using CHIRACEL AD column eluting with heptanes/i-PrOH (9/1) to afford the desired first eluting isomer diethyl(1S,2S,3R,4S)-3-(2-methylphenyl)-4-hydroxycyclohexane-1,2-dicarboxylate according to the procedure of Example 6, Step D.

Step H: Diethyl(1S,2S,3R,4S)-4-{(1R)-1-[3,5-bis(trifluoromethyl)phenyl]ethoxy}-3-(2-methylphenyl)cyclohexane-1,2-dicarboxylate The title compound was prepared from the first eluting isomer diethyl(1S,2S,3R,4S)-3-(2-methylphenyl)-4-hydroxycyclohexane-1,2-dicarboxylate (step G) and (1S)-1-[3,5-bis(trifluoromethyl)phenyl]ethyl-2,2,2-trichloroethanimidoate (Example 6, step E) according to the procedure of Example 6, step F. $^1$H-NMR (CDCl$_3$): δ: 7.65 (1 H, s), 7.15 (2 H, s), 7.08-6.92 (4 H, m), 4.25 (1 H, q, J=6.0 Hz), 4.20-4.10 (2 H, m), 3.85-3.66 (2 H, m), 3.42 (1 H, m), 3.21 (1 H, t), 2.90-2.79 (2 H, m), 2.35 (1 H, m), 2.25 (1 H, m), 2.22 (3 H, s), 1.69-1.56 (2 H, m), 1.30 (3 H, d, J=6.0 Hz), 1.23 (3 H, t, J=7.2 Hz), 0.77 (3 H, t, J=7.2 Hz). Unreacted starting alcohol could be recovered by flushing the column with EtOAc and reused in the above reaction.

Step I: [(1S,2R,3R,4S)-4-{(1R)-1-[3,5-bis(Trifluoromethyl)phenyl]ethoxy}-3-(2-methylphenyl)cyclohexane-1,2-diyl]dimethanol The title compound was prepared from the intermediate of step H according to the procedure of Example 6, step G. $^1$H-NMR (CDCl$_3$): δ: 7.64 (1 H, s), 7.16 (2 H, s), 7.04-6.91 (4 H, m), 4.24 (1 H, q, J=6.0 Hz), 3.74 (1 H, m), 3.60 (1 H, m), 3.48 (1 H, m), 3.35-3.20 (2 H, m), 2.90-2.70 (2H, m), 2.26 (1 H, m), 2.21 (3 H, s), 1.85 (1 H, m), 1.62 (1 H, m), 1.56-1.42 (3 H, m), 1.28 (3 H, t, J=6.0 Hz).

Step J: [(1S,2R,3R,4S)-4-{(1R)-1-[3,5-bis(Trifluoromethyl)phenyl]ethoxy}-3(2methylphenyl)cyclohexane-1,2-diyl]di(methylene)dimethanesulfonate The title compound was prepared from the intermediate of Step I according to the procedure of Example 6, step H and used without further purification.

Step K: (3aR,4R,5S,7aS)-2-Benzyl-5-{(1R)-1-[3,5-bis(trifluoromethyl)phenyl]ethoxy}-4-(2-methylphenyl)octahydro-1H-isoindole The title compound was prepared from the intermediate step J and benzylamine according to the procedure of Example 6, step I. $^1$H-NMR (CDCl$_3$): δ: 7.64 (1 H, s), 7.32-7.25 (5 H, m), 7.18 (2 H, s), 7.04-6.97 (4 H, m), 4.25 (1 H, q, J=6.0 Hz), 3.75 (1 H, d, J=13.4 Hz), 3.65 (1 H, d, J=13.4 Hz), 3.40 (1 H, m), 2.90 (2 H, m), 2.54-2.30 (4 H, m), 2.22 (3 H, s), 2.02-1.85 (3 H, m), 1.61 (1 H, m), 1.33 (3 H, t, J=6.0 Hz), 1.30 (1 H, m).

Step L: (3aR,4R,5S,7aS)-5-{(1R)-1-[3,5-bis(Trifluoromethyl)phenyl]ethoxy}-4(2-methylphenyl)octahydro-1H-isoindole The title compound was prepared from the intermediate step K according to the procedure of Example 6, step J. $^1$H-NMR (CDCl$_3$): δ: 7.64 (1 H, s), 7.18 (2 H, s), 7.04-6.97 (4 H, m), 4.25 (1 H, q, J=6.5 Hz), 3.40 (1 H, m), 3.25 (1 H, m), 2.90-2.75 (2 H, m), 2.63 (1 H, t), 2.44 (1 H, t), 2.35 (1 H, m), 2.22 (3 H, s), 2.05 (1 H, m), 1.86-1.72 (2 H, m), 1.61 (1 H, m), 1.33-1.20 (5 H, m).

Step M: 3-[(3aR,4R,5S,7aS)-5-{(1R)-1-[3,5-bis(Trifluoromethyl)phenyl]ethoxy}-4-(2--methylphenyl)-octahydro-2H-isoindol-2-yl]cyclopent-2-en-1-one The title compound was prepared from (3aR,4R,5S,7aS)-5-{(1R)-1-[3,5-bis(trifluoromethyl)phenyl]ethoxy}-4-(2-methylphenyl)octahydro-1H-isoindole (step L) and cyclopentane-1,3-dione according to the procedure of Example 7. $^1$H-NMR (CDCl$_3$): rotamers δ: 7.64 (1 H, s), 7.18 (2 H, s), 7.04-6.97 (4 H, m), 4.74, 4.53 (1 H, s), 4.42 (1 H, m), 3.68, 3.43 (1 H, m), 3.50 (1 H, m), 3.06 (1 H, m), 2.93 (2 H, m), 2.86, 2.76 (1 H, m), 2.57 (1 H, m), 2.40 (2 H, m), 2.28 (3 H, s), 2.20 (1 H, m), 2.17 (1 H, m), 2.10-1.94 (3 H, m), 1.58 (1 H, m), 1.40 (1 H, m), 1.28 (3 H, d, J=6.0 Hz). MS: (MH)$^+$ 552.43

Using the procedures essentially comparable to those described above the compounds of the following Examples were prepared.

| Ex. # | R¹ | X | parent ion (MH⁺) m/z |
|---|---|---|---|
| 12 | -C(=O)CH₃ | F | 518.45 |
| 13 | -CH₂CH₂-phenyl | F | 580.0 |
| 14 | -CH₂CH₂CH₂-OH (HOCH₂CH₂CH₂-) | F | 520.1 |
| 15 | -C(=O)NHCH₃ | F | 533.59 |

Using the procedures essentially comparable to those described above the compounds of the following Examples were prepared.

| Ex. # | R¹ | X | parent ion (MH⁺) m/z |
|---|---|---|---|
| 16 | -C(=O)CH₃ | F | 518.28 |
| 17 | Me | F | 490.25 |
| 18 | 4-oxocyclopent-2-en-1-yl | H | 538.7 |
| 19 | 4-oxo-2-hydroxy-cyclopent-2-en-1-yl (OH) | F | 572.5 |
| 20 | 4-oxo-2-hydroxy-cyclopent-2-en-1-yl (OH) | F | 572.5 |
| 21 | 4-oxo-5-hydroxy-cyclopent-2-en-1-yl | F | 572.5 |
| 22 | 4-oxo-5-hydroxy-cyclopent-2-en-1-yl | F | 572.5 |
| 23 | 2-methyl-4-oxo-cyclopent-2-en-1-yl | F | 570.0 |

-continued

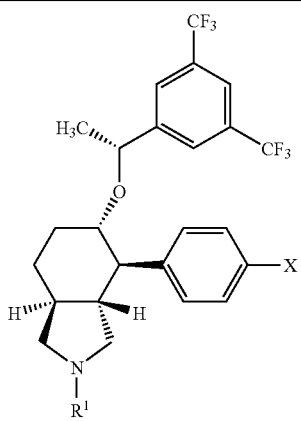

| Ex. # | R¹ | X | parent ion (MH⁺) m/z |
|---|---|---|---|
| 24 | —C(O)—NH—CH₃ | F | 533.05 |
| 25 | —C(O)—NH₂ | F | 519.0 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A method for treating or preventing a disorder of bladder function in a human patient in need of such treatment or prevention, comprising administering to the patient a therapeutically effective amount of a compound of formula I:

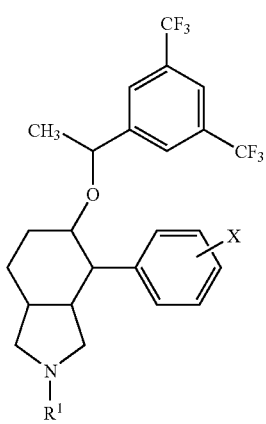

wherein:
R¹ is selected from the group consisting of:
  (1) hydrogen,
  (2) $C_{1-6}$alkyl, which is unsubstituted or substituted with halogen, hydroxyl or phenyl,
  (3) cyclopentenone, which is unsubstituted or substituted with hydroxyl or methyl,
  (4) —(CO)—C$_{1-6}$alkyl,
  (5) —(CO)—NH$_2$,
  (6) —(CO)—NHC$_{1-6}$alkyl, and
  (7) —(CO)—N(C$_{1-6}$alkyl)(C$_{1-6}$alkyl);
  (1) hydrogen,
  (2) fluorine, and
  (3) methyl;
and pharmaceutically acceptable salts thereof and individual enantiomers and diastereomers thereof.

2. The method according to claim 1 wherein the compound of formula I is

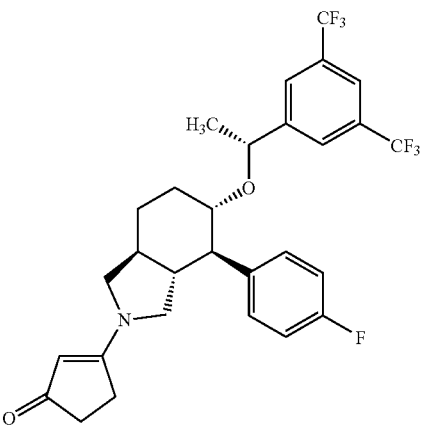

or a pharmaceutically acceptable salt thereof.

3. The method according to claim 2 wherein the disorder of bladder function is cystitis.

4. The method according to claim 2 wherein the disorder of bladder function is bladder detrusor hyper-reflexia.

5. The method according to claim 2 wherein the disorder of bladder function is frequent urination.

6. The method according to claim 2 wherein the disorder of bladder function is urinary incontinence.

7. The method according to claim 2 wherein the disorder of bladder function is overactive bladder with one or more of the symptoms of urge urinary incontinence, urgency or frequency.

* * * * *

UNITED STATES PATENT AND TRADEMARK OFFICE
CERTIFICATE OF CORRECTION

PATENT NO.         : 7,345,083 B2
APPLICATION NO.    : 11/714352
DATED              : March 18, 2008
INVENTOR(S)        : Jaime Lynn Bunda et al.

It is certified that error appears in the above-identified patent and that said Letters Patent is hereby corrected as shown below:

Column 36, line 10, "(4) —(CO)—Cl$_{1-6}$alkyl," should read --(4) —(CO)—C$_{1-6}$alkyl,--.

Column 36, line 14, after "(7) —(CO)—N(C$_{1-6}$alkyl)(C$_{1-6}$alkyl);" insert --X is independently selected from the group consisting of:--.

Signed and Sealed this

Twenty-fourth Day of November, 2009

David J. Kappos
*Director of the United States Patent and Trademark Office*